(12) United States Patent
Kammel et al.

(10) Patent No.: US 7,839,981 B2
(45) Date of Patent: Nov. 23, 2010

(54) ANTI-SCATTER GRID

(75) Inventors: Johanna Kammel, Ettersburg (DE);
Sebastian Köppl, Petersaurach (DE);
Marc Ordung, Erlangen (DE);
Bernhard Roas, Möhrendorf (DE);
Peter Strattner, Heilsbronn (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/326,641

(22) Filed: Dec. 2, 2008

(65) Prior Publication Data
US 2009/0147923 A1 Jun. 11, 2009

(30) Foreign Application Priority Data
Dec. 7, 2007 (DE) .................. 10 2007 058 986

(51) Int. Cl.
*G21K 1/00* (2006.01)
*G21K 1/02* (2006.01)

(52) U.S. Cl. ..................... 378/154; 378/149
(58) Field of Classification Search .............. 378/145, 378/147–155
See application file for complete search history.

(56) References Cited

U.S. PATENT DOCUMENTS

| | | | |
|---|---|---|---|
| 6,801,600 B2 * | 10/2004 | Kohda ........... | 378/154 |
| 6,980,629 B1 | 12/2005 | Hoheisel et al. | |
| 2006/0055087 A1 | 3/2006 | Freund et al. | |

FOREIGN PATENT DOCUMENTS

| | | |
|---|---|---|
| DE | 102 41 424 A1 | 3/2004 |
| DE | 10 2004 027 158 A1 | 12/2005 |

OTHER PUBLICATIONS

German Office Action dated Aug. 27, 2008 with English translation.

* cited by examiner

*Primary Examiner*—Irakli Kiknadze
(74) *Attorney, Agent, or Firm*—Brinks Hofer Gilson & Lione

(57) ABSTRACT

An anti-scatter grid for medical x-ray devices is provided. The anti-scatter grid comprising a number of first elements from a first material with second elements made from a second material integrated therein. In this case the first material is more transparent to radiation than the second material. The second elements are arranged in the first elements such that for stacking of the first elements a grid absorbing scattered radiation is formed by means of second elements for radiation arriving perpendicular to the direction of the stacking of the first elements. The advantage of this is that this anti-scatter grid is able to be produced simply and reliably with a large aspect ratio.

20 Claims, 5 Drawing Sheets

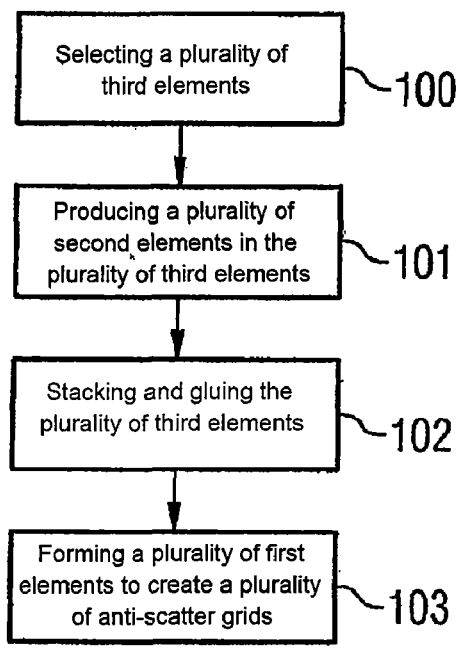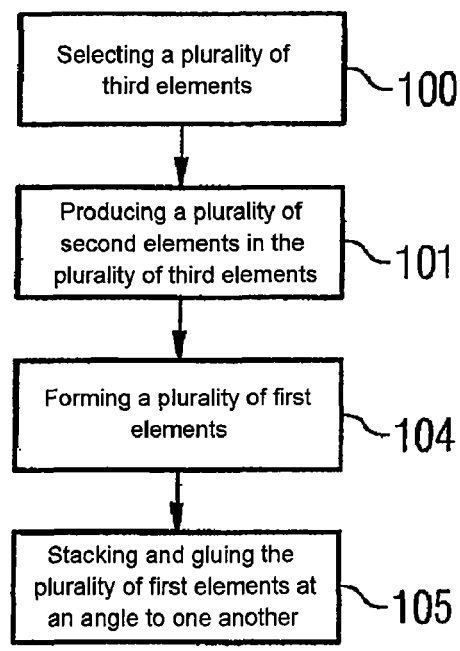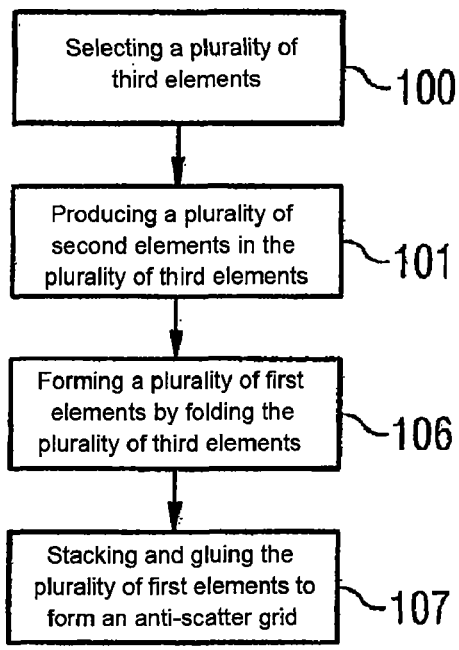

ANTI-SCATTER GRID

The present patent document claims the benefit of German Patent Application DE 10 2007 058 986.9 filed on Dec. 7, 2007, which is incorporated by reference.

The present embodiments relate to an anti-scatter grid constructed from a number of elements.

X-ray imaging technology imposes high demands on the image quality of the x-ray images. To produce images, such as images produced in medical diagnostics, an object to be examined is illuminated by x-ray radiation of an approximately point-type x-ray source and the distribution of the attenuation of the x-ray radiation is detected two-dimensionally on the side of the object opposite to the x-ray source. A row-by-row detection of the x-ray radiation attenuated by the object can be undertaken in computer tomography systems, for example. In addition to x-ray films and gas detectors, solid-state detectors are increasingly being used as x-ray detectors. The detectors generally have a matrix-type arrangement of optoelectronic semiconductor components as opto-electric receivers. Each pixel of the x-ray image should correspond to an attenuation of the x-ray radiation through the object on a straight-line axis from the point-type x-ray source to the location corresponding to the pixel of the detector surface. X-rays that arrive in a straight line from the point-type x-ray source on this axis at the x-ray detector are referred to as primary rays.

The x-ray radiation emitted by the x-ray source is scattered in the object because of inevitable interactions, so that the primary rays and secondary radiation hits the detector. The scattered radiation, which depending on the characteristics of the object with diagnostic images can cause more than 90% of the entire signal modulation of an x-ray detector, represents a source of noise and reduces the ability to detect fine differences in contrast.

To reduce the proportion of scattered radiation falling on the detector plane, anti-scatter grids are used between the object and the detector. Anti-scatter grids include regularly-arranged structures absorbing the x-ray radiation, between which passage channels or passage slots for the most unattenuated possible passage of the primary radiation are embodied. With focused anti-scatter grids, these passage channels or passage slots are focused according to the distance to the point-type x-ray source, for example, the distance to the focus of the x-ray tube. With non-focused anti-scatter grids, the passage channels or passage slots are aligned over the entire surface of the anti-scatter grid perpendicular to the surface. This alignment leads to a perceptible loss of primary radiation at the edges of the recorded image, since at these points a greater part of the incident primary radiation hits the absorbent area of the anti-scatter grid.

To achieve a high image quality, high demands are imposed on the characteristics of x-ray anti-scatter grids. The anti-scatter grids are to absorb the scattered rays as well as possible and allow a highest possible proportion of primary radiation to pass unattenuated through the anti-scatter grid. The scattered radiation falling on the detector surface can be reduced by a high ratio of the height of the anti-scatter grid to the thickness or the diameter of the passage channels or passage slots, for example, through a high aspect ratio. Because of the thickness of the absorbent structures or wall elements lying between the passage channels or passage slots, however, image faults can arise through absorption of a part of the primary radiation. When solid-state detectors are used in homogeneities of the grid, deviations of the absorbent areas from their ideal position lead to image faults through mapping of the grid in the x-ray image. With detector elements arranged in the form of a matrix, for example, there is the danger of the projection of the structures of detector elements and anti-scatter grid interfering with each other. This results in the occurrence of disruptive moiré appearances.

The absorbent structure elements of anti-scatter grids cannot be produced thin enough or precisely enough. Accordingly, a significant part of the primary radiation is removed by these structure elements.

The same problem arises in nuclear medicine, especially in the application of gamma cameras, such as Anger cameras, for example. With this imaging technique, in a similar way to x-ray diagnostics, as few scattered gamma quanta as possible should reach the detector. By contrast with x-ray diagnostics, in nuclear diagnostics, the radiographic source for the gamma quanta is within the object. The patient is injected with a specific metabolic preparation marked with unstable nuclides. The specific metabolic preparation then builds up in specific organs. An image of the organ is then obtained through detection of the corresponding decay quanta emitted from the body. The time gradient of the activity in the organ allows conclusions to be drawn about its function. To obtain an image of the inside of the body, a collimator is used in front of the gamma detector that determines the direction of projection of the image. The collimator corresponds in its functions and structure to the anti-scatter grid in x-ray diagnostics. The gamma quanta determined by the preferred direction of the collimator can pass through the collimator, quanta arriving at an angle to the collimator are absorbed in the collimator walls. Because of the higher energy of the gamma quanta by comparison with x-ray quanta collimators is designed to be a multiple higher than anti-scatter grids for x-ray radiation.

Accordingly, quanta scattered during imaging is selected out by quanta of a specific energy being taken into account in the image. However, each detected scattered quantum causes a dead time of the gamma camera of, for example, one microsecond, during which no further events are able to be registered. When a primary quantum arrives shortly after the registration of a scatter quantum, the primary quantum cannot be registered and is lost for the image. If a scatter quantum coincides in time, within certain limits, with a primary quantum, a similar effect occurs. Since the evaluation electronics can then no longer separate the two events, too high an energy is determined and the event will not be registered. The two cases given explain that a highly effective scattered radiation suppression also leads in nuclear diagnostics to an improved quantum efficiency. In the final analysis this allows an improved image quality to be achieved with the same dosing of the applied radio nuclide or makes a smaller radio-nuclide dose possible with the same image quality, so that the patient's exposure to radiation is reduced and shorter imaging times can be achieved.

There are different techniques and corresponding embodiments for producing anti-scatter grids for x-ray radiation and collimators for gamma radiation. For example, patent application DE 102 41 424 A1 describes various production methods and embodiments of anti-scatter grids.

SUMMARY AND DESCRIPTION

The present embodiments may obviate one or more of the drawbacks or limitations inherent in the related art. For example, in one embodiment, an anti-scatter grid can be produced simply and at low cost even with a high aspect ratio.

In one embodiment, an anti-scatter grid includes a number of first elements, for example, made of a plastic foil, of a first material with second elements made of a second material integrated into them. The first material is more transparent to radiation than the second material. Accordingly, radiation is more strongly attenuated in its passage through the second material than in its passage through the first material. The second elements are integrated into the first elements. Accordingly, when the first elements are stacked on top of one another, a grid absorbing the scattered radiation for radiation entering perpendicular to the direction of the stacking of the first elements can be formed by the second elements.

Microstructures may be produced for forming a grid with a very large aspect ratio.

The first elements may be cuboids and stacked on each other with the two largest congruent surfaces. The radiation enters perpendicular to the longer side of the surface. Accordingly, a stack of first elements may be constructed in a simple manner.

In a further embodiment, the second elements of the two or more first elements are arranged above one another. This produces a grid not focusing in this dimension.

The second elements may be strips or ribs. The second elements may be arranged in parallel to the stack surfaces of the first elements at an angle to the perpendicular of the direction of the stack, with the angle continuously changing from one edge of the first element to the other. A focus effect can be created in this dimension.

Furthermore the second elements can be formed by local removal of the first material and filling the pits produced with the second material.

The pits may be formed using a photo lithographic method and filled with the second material using an electrical method. Accordingly, production methods may be used.

In a further embodiment, the second material may have a higher atomic number than the first material. The radiation-absorbing effect of the anti-scatter grid is produced in this way.

The first element may include plastic foil and the height of the second element may be at least 50% of the thickness of the plastic foil. This allows easily-stackable first elements with a large aspect ratio to be produced.

In a further embodiment, the first elements may be connected to each other by an adhesive. The individual first elements are held together in this way.

In a development the first elements can be stacked into the direction of radiation at an angle by which a focusing effect is able to be achieved.

In one embodiment, a collimator for gamma rays is provided. The anti-scatter grid described above may be employed for use as a collimator for gamma radiation. Accordingly, collimators with a large aspect ratio can also be produced in a simple manner.

In other embodiments, a number of methods for production of the anti-scatter grid are provided. An associated computer program product is also provided.

In one embodiment, a method act for production of an anti-scatter grid is provided. The method includes selection of third elements from which a plurality of first elements is able to be formed by separation or by cutting, production of second elements in the third elements with the second elements forming a repeating structure spaced at the width of the first elements, stacking and connecting, preferably through gluing, of the third elements into a block-like module, and separation of the block-like module spaced at the width of the first elements, which produces a number of anti-scatter grids from stacked first elements. One advantage of this method is the simple, precise and simultaneous production of a plurality of anti-scatter grids.

In another embodiment, a further method act includes selection of third elements from which a plurality of first elements is able to be formed by separation or by cutting, producing second elements in the third elements with the second elements forming a repeating structure spaced at the width of the first elements, separation of the third elements spaced at the width of the first elements which produces a number of first elements, and stacking and connecting, preferably through gluing, of the first elements at an angle to each other into a block-like module which forms the anti-scatter grid. This enables an anti-scatter grid focusing in two dimensions to be produced.

In another embodiment, a further method act includes selection of a third element from which a plurality of first elements is able to be formed by folding, producing second elements in the third elements with the second elements forming a repeating structure spaced at the width of the first elements, folding of the third elements spaced at the width of the first element, and stacking and connecting, preferably through gluing, of the first elements into a block-like module which forms the anti-scatter grid. This enables an anti-scatter grid to be produced in a simple manner from a foliar third element.

In one embodiment, a computer program product includes a computer program which includes software for executing one of the production methods, if the computer program is executed in an anti-scatter grid production facility.

BRIEF DESCRIPTION OF THE DRAWINGS

FIG. 7 illustrates a flowchart of one embodiment of a production method, FIG. 8 illustrates a flowchart of another embodiment of a production method, and FIG. 9 illustrates a flowchart of another embodiment of a production method.

DETAILED DESCRIPTION

Figure 1:
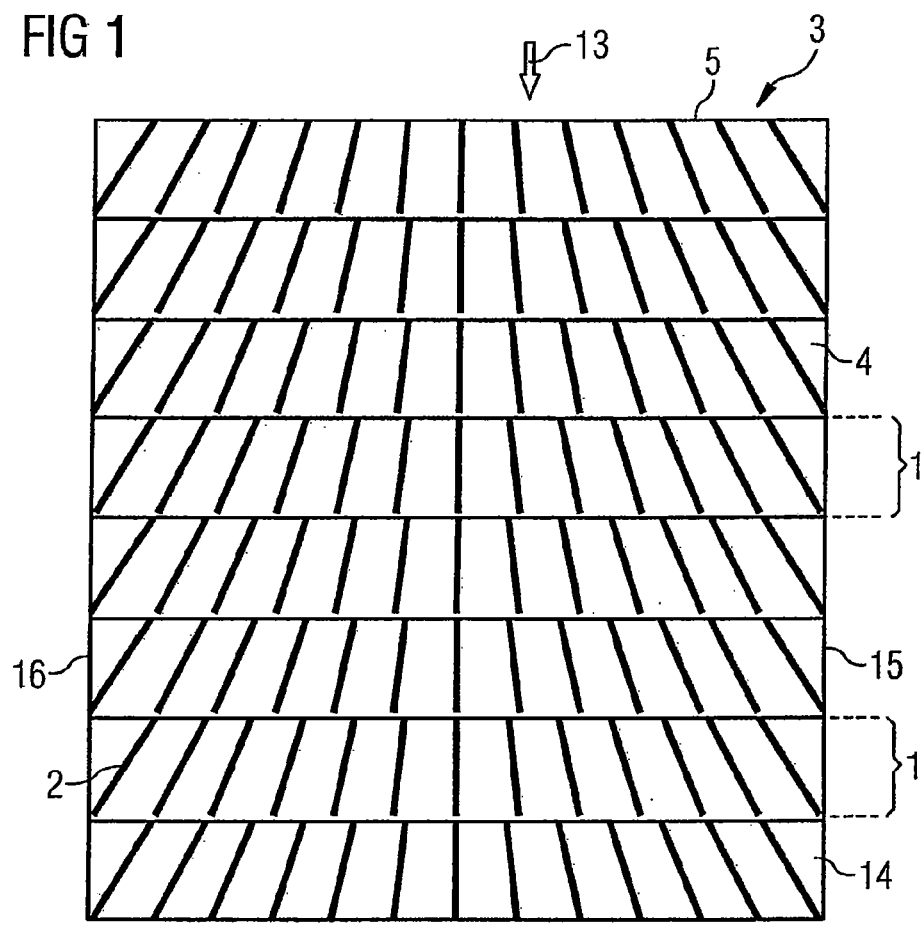
FIG. 1 illustrates one embodiment of a third element of an anti-scatter grid.

FIG. 1 shows a view from above a third element 3, for example, a plastic foil. Integrated into the plastic foil 3 are regularly-repeating second elements 2, such as microstructures. A number of second elements 2 form a first element 1. The second elements 2 are arranged in the radiation direction 13 with an angle 14 to the lateral edge 15 of the plastic foil 3. The angle 14 decreases continuously towards the middle of the plastic foil 3 or towards the middle of the first element 1 and then increases back to the second edge 16 again. A focus effect of an anti-scatter grid 10 formed therefrom in the direction of radiation 13, perpendicular to the width 5 of the third element 3, can be achieved.

Figure 2:
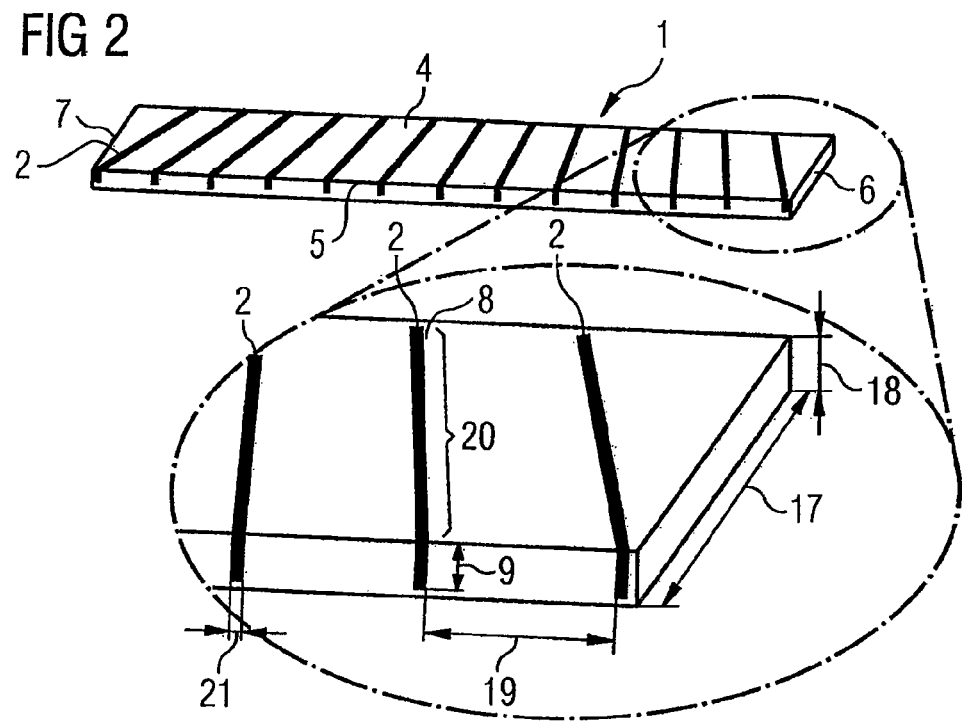
FIG. 2 illustrates one embodiment of a first element of an anti-scatter grid.

The plastic foil 3 has, for example, a width of 400 mm and a thickness of between 0.1 and 0.5 mm FIG. 2 shows a part of the third element 3 of one of the first elements 1, and a detailed view thereof. Located in the first element 1 are pits 8, in which the second elements 2 absorbing scattered radiation are arranged. The pits 8 have an average spacing 19 from one another, an average length 20, a depth 9 and a pit width 21. The first element 1 consists of a first material, has a width 17 and a height 18 and is preferably made of a plastic foil. For an optimum scattered radiation attenuation, the pit depths 9 should be at least 50% of the height 18 of the first element 1, or of the foil thickness. The pit depth 9 may be limited in the final analysis by the required minimum stability during the production of the pits 8 and the integration of the second elements 2. A ratio of around 1:10:100 may be used for the ratio of pit width 21 to average spacing 19 of the pits and to the average length 20 of the pits.

The pits 8 may be created by different structuring techniques, for example, photolithography, by first material being etched out of the first element 1. The pits 8 are then filled, using a galvanic method, for example, with a second material and thus form the second element 2.

Figure 3:
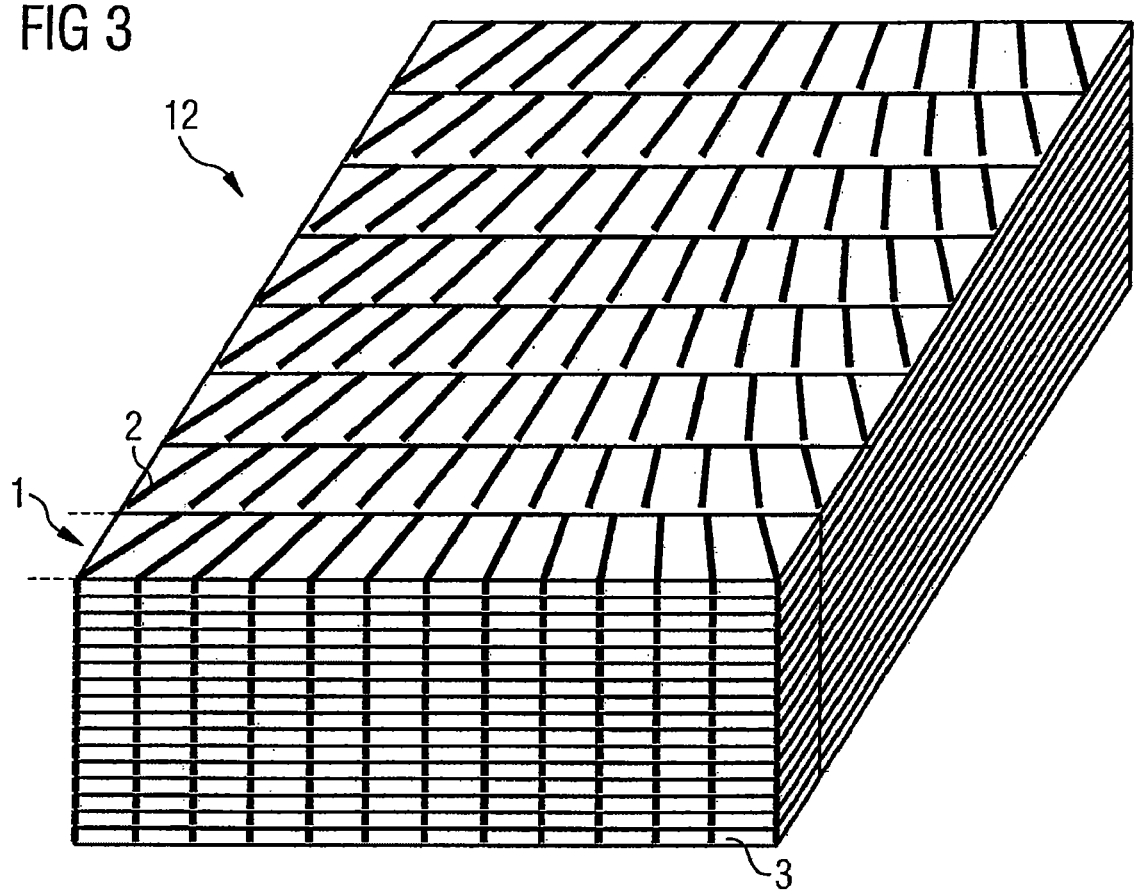
FIG. 3 illustrates one embodiment of a block-like module embodied from a plurality of first elements.

FIG. 3 shows a plurality of third elements 3, for example, plastic foils, which are stacked above one another and thus form a module 12, such as a block-like structure. The third elements 3 are stacked so that the second elements integrated within them lie directly above one another. The third elements 3 are fixed together, for example, glued together.

Figure 4:
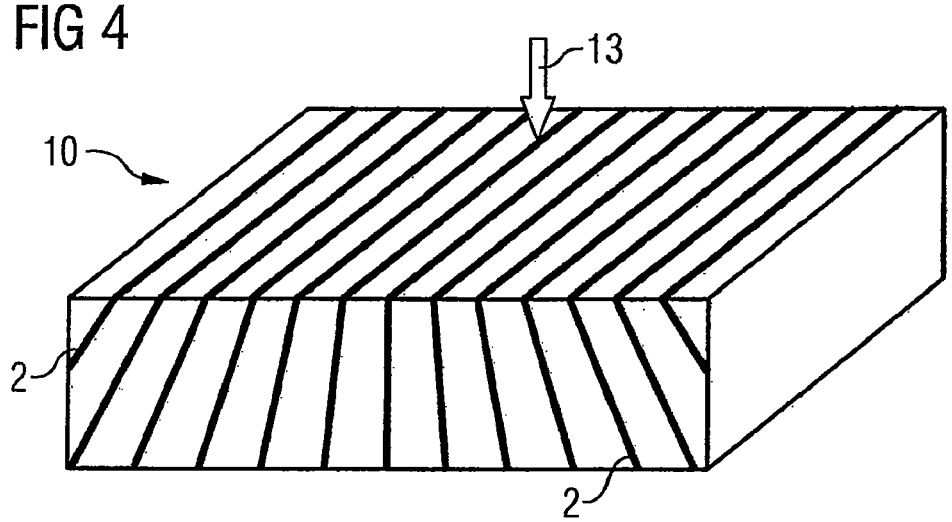
FIG. 4 illustrates one embodiment of an anti-scatter grid.

By separating the module 12 along the first elements 1, an anti-scatter grid 10, as is shown in the example of FIG. 4, is produced. The absorption effect of the second elements 2 may be produced for radiation arriving from the direction 13.

Figure 5:
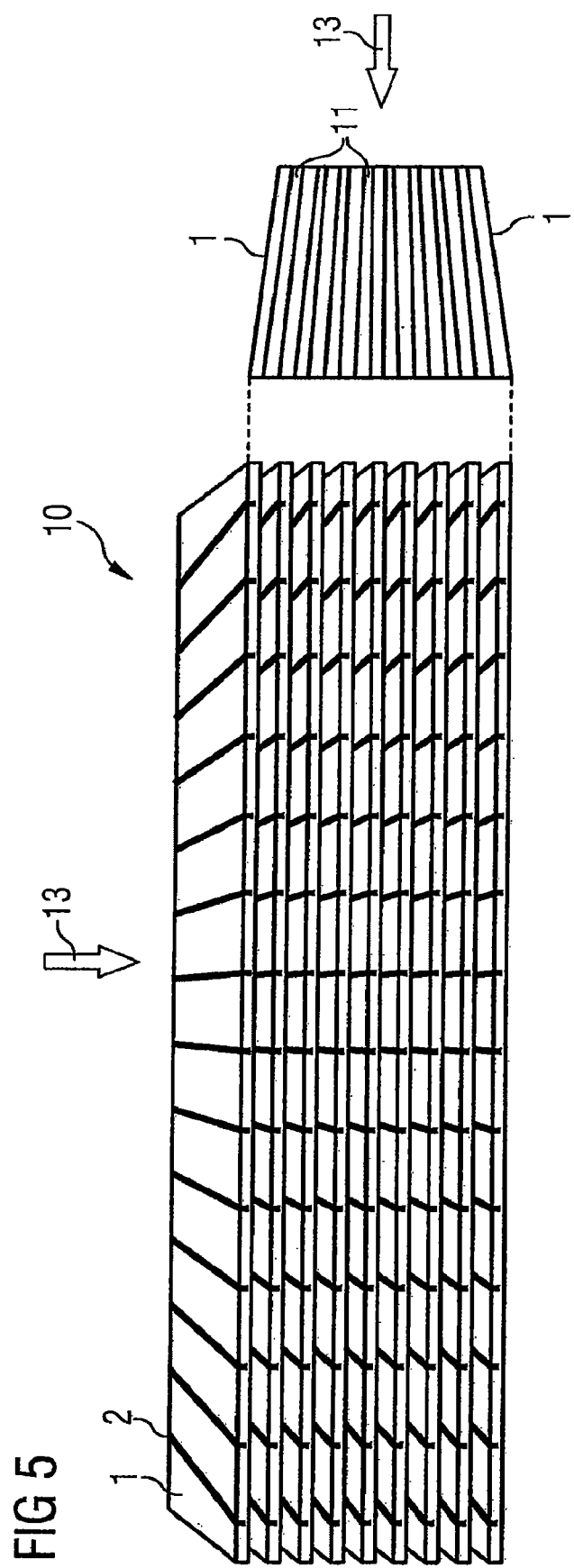
FIG. 5 illustrates another embodiment of a further anti-scatter grid.

FIG. 5 shows an anti-scatter grid 10 including first elements 1 with second elements integrated therein, which are stacked at an angle to each other and glued together with an adhesive 11. This produces an additional focus effect for the radiation 13 in a second dimension. The radiation again arrives perpendicular to the direction of the stack from direction 13 into the anti-scatter grid 10.

Figure 6:
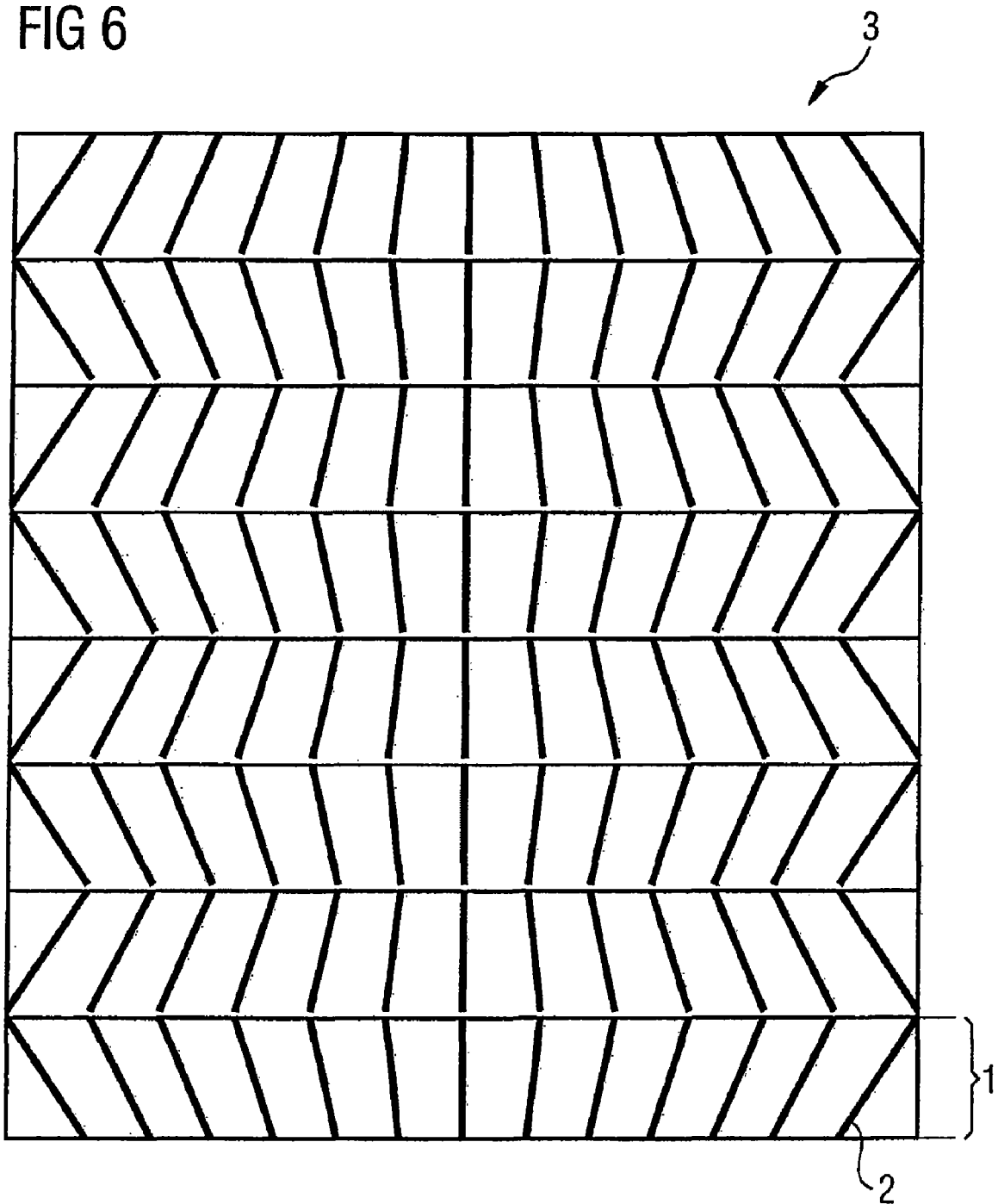
FIG. 6 illustrates another embodiment of a further third element.

FIG. 6 shows a third element 3. By folding along the boundaries of the first elements 1 of the third element 3 and subsequent stacking, an anti-scatter grid 10 is able to be produced. The second elements 2 are mirrored alternately in rows corresponding to the first elements 1.

FIGS. 7 and 8 show flowcharts for producing anti-scatter grids 10.

FIG. 7 describes a production method, with, in act 100, third elements 3 being selected from which, by separation, for example, by cutting, a plurality of first elements 1 is able to be formed. In act 101 second elements 2 are produced in the third elements 3, with the second elements 2 forming a repeating structure spaced at the width 17 of the first elements 1. Subsequently, in act 102, the third elements 3 are stacked into a module 12 and glued. Finally, in act 103 the module 12 is separated spaced at the width 17 of the first elements 1, where a number of anti-scatter grids 10 are created from stacked first elements 1.

FIG. 8 describes a production method in which anti-scatter grids 10 are able to be produced in a second focusing effect direction. In the first act 100 third elements 3 are selected, from which by separation, for example by cutting, a plurality of first elements 1 is able to be formed. In act 101, second elements 2 are produced in the third elements 3, with the second elements 2 forming a repeating structure spaced at the width 17 of the first elements 1. Subsequently the third elements 3 are cut and separated spaced at the width 17 of the first elements 1 in act 104, which produces a number of first elements 1. In the concluding act 105 the first elements 1 thus produced are stacked at an angle to each other and glued together, which forms the anti-scatter grid 10.

FIG. 9 shows the execution sequence of a further production method beginning with act 100, in which a third element 3 is selected, from which a plurality of first elements 1 is able to be formed by folding 106. In the subsequent act 101 second elements 2 are created in the third element 3, with the second elements 2 forming a repeating structure spaced at the width 17 of the first elements 1. In act 106 the third element 3 is folded spaced at the width 17 of the first element 1, and in the final act 107 the first elements 1 thus produced are stacked and glued together, which forms the anti-scatter grid 10.

Collimators for gamma radiation are produced in a similar manner.

Various embodiments described herein can be used alone or in combination with one another. The foregoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. An anti-scatter grid for medical x-ray devices, the anti-scatter grid comprising:
    a number of first elements made of a first material with second elements made of a second material integrated therein, the first material being more transparent to radiation than the second material,
    wherein the second elements are arranged in the first elements such that, when the first elements are stacked, a grid absorbing scattered radiation is able to be formed by the second elements for radiation arriving perpendicular to the direction of the stacking of the first elements, and
    wherein the second elements are formed by local removal of the first material and filling pits produced by the local removal of the first material with the second material.

2. The anti-scatter grid as claimed in claim 1, wherein the first elements are cuboid and are stacked on the two largest congruent surfaces, with the radiation arriving perpendicular to the longer side of the congruent surfaces.

3. The anti-scatter grid as claimed in claim 1, wherein the second elements of the two or more first elements are arranged above one another.

4. The anti-scatter grid as claimed in claim 1, wherein the second elements are strips or ribs which are arranged at an angle perpendicular to the direction of stacking, with the angle continuously changing from one edge of the first element to the other edge.

5. The anti-scatter grid as claimed in claim 1, wherein the pits are able to be formed using a photolithographic method and the pits are able to be filled by a galvanic method.

6. The anti-scatter grid as claimed in claim 1, wherein the second material has a higher atomic number than the first material.

7. The anti-scatter grid as claimed in claim 1, wherein the first element comprises a plastic foil and the height of the second elements is at least 50% of the thickness of the plastic foil.

8. The anti-scatter grid as claimed in claim 1, wherein the first elements are connected to each other by an adhesive.

9. The anti-scatter grid as claimed in claim 1, wherein the first elements are stacked in a direction of radiation in relation to each other at an angle so that a focusing effect is able to be achieved.

10. A collimator for gamma radiation, the collimator including:
    a number of first elements made of a first material with second elements made of a second material integrated therein, the first material being more transparent to radiation than the second material,
    wherein the second elements are arranged in the first elements such that, when the first elements are stacked, a grid absorbing scattered radiation is able to be formed by the second elements for radiation arriving perpendicular to the direction of the stacking of the first elements, and wherein the second elements are formed by local removal of the first material and filling pits produced by the local removal of the first material with the second material.

11. The collimator as claimed in claim 10, wherein the first elements are cuboid and are stacked on the two largest congruent surfaces, with the radiation arriving perpendicular to the longer side of the congruent surfaces, and wherein the grid is an anti-scatter grid.

12. The collimator as claimed in claim 10, wherein the second elements are strips or ribs which are arranged at an angle perpendicular to the direction of stacking, with the angle continuously changing from one edge of the first element to the other edge, and wherein the gird is an anti-scatter grid.

13. The collimator as claimed in claim 10, wherein the first elements are stacked in a direction of radiation in relation to each other at an angle so that a focusing effect is able to be achieved, and wherein the grid is an anti-scatter grid.

14. A method for production of an anti-scatter grid, the method including:

selecting third elements from which a plurality of first elements are able to be formed by separation or by cutting, producing second elements in the third elements with the second elements forming a repeating structure spaced at the width of the first elements, stacking and connecting of the third elements into a module, and separating the module spaced at the width of the first elements, which produces a number of anti-scatter grids from stacked first elements.

15. The method for production as claimed in claim 14, further comprising:

selecting third elements from which by separation or by cutting a plurality of first elements is able to be formed, producing second elements in the third elements with the second elements forming a repeating structure spaced at the width of the first elements, separating the third elements spaced at the width of the first elements which produces a number of first elements, and stacking and connecting of the first elements at an angle to each other, which forms the anti-scatter grid.

16. The method for production as claimed in claim 15, wherein stacking and connecting includes gluing.

17. A method for production of an anti-scatter grid, the method including:

selecting a third element from which a plurality of first elements is able to be formed by folding, producing second elements in the third element with the second elements forming a repeating structure spaced at the width of the first elements, folding of the third element spaced at the width of the first element, and stacking and connecting of the first elements, which forms the anti-scatter grid.

18. The method for production as claimed in claim 17, wherein stacking and connecting includes gluing.

19. A computer program product with a computer program, the computer program including software such that when the computer program is executed in an anti-scatter grid production facility the computer program is operable to:

select third elements from which a plurality of first elements are able to be formed by separation or by cutting, produce second elements in the third elements with the second elements forming a repeating structure spaced at the width of the first elements, stack and connect the third elements into a module, and separate the module spaced at the width of the first elements, which produces a number of anti-scatter grids from stacked first elements.

20. The computer program product of claim 19, wherein the computer program is operable to:

select third elements from which by separation or by cutting a plurality of first elements is able to be formed, produce second elements in the third elements with the second elements forming a repeating structure spaced at the width of the first elements, separate the third elements spaced at the width of the first elements which produces a number of first elements, and stack and connect the first elements at an angle to each other, which forms the anti-scatter grid.

\* \* \* \* \*